United States Patent [19]

Watanabe et al.

[11] Patent Number: 5,009,813
[45] Date of Patent: Apr. 23, 1991

[54] COMPOSITION FOR HAIR TREATMENT AGENT

[75] Inventors: Taichi Watanabe, Ichikawa; Hidekazu Ogino, Tokyo; Hajime Hirota, Tokyo; Tomohito Koshika, Tokyo; Naoko Moriya, Tokyo; Toshio Nozaki, Sakura, all of Japan

[73] Assignee: Kao Corporation, Tokyo, Japan

[21] Appl. No.: 344,443

[22] Filed: Apr. 27, 1989

Related U.S. Application Data

[63] Continuation of Ser. No. 122,454, Nov. 19, 1987, abandoned.

[30] Foreign Application Priority Data

Nov. 28, 1986 [JP] Japan ................................ 61-283745
Dec. 15, 1986 [JP] Japan ................................ 61-297897
Dec. 16, 1986 [JP] Japan ................................ 61-299673

[51] Int. Cl.$^5$ .................................................. C11D 1/02
[52] U.S. Cl. .................................... 252/545; 252/546; 252/547; 252/DIG. 13; 252/DIG. 2; 252/DIG. 5; 8/127.51; 424/70; 424/78
[58] Field of Search ........ 252/DIG. 13, 547, DIG. 5, 252/DIG. 2, 545, 546; 132/209; 8/127.51; 424/70

[56] References Cited

U.S. PATENT DOCUMENTS

| | | | |
|---|---|---|---|
| 4,009,256 | 2/1977 | Nowak, Jr. et al. | 424/70 |
| 4,180,084 | 12/1979 | Wegmuller et al. | 132/7 |
| 4,220,548 | 9/1980 | Mashimoto et al. | 252/106 |
| 4,272,517 | 6/1981 | Yoneda et al. | 424/72 |
| 4,273,760 | 6/1981 | Koehler et al. | 424/70 |
| 4,329,334 | 5/1982 | Su et al. | 424/70 |
| 4,362,528 | 12/1982 | Grollier et al. | 8/406 |
| 4,364,837 | 12/1982 | Pader | 252/173 |
| 4,391,286 | 7/1983 | Hsiung et al. | 132/7 |
| 4,445,521 | 5/1984 | Grollier et al. | 8/406 |
| 4,477,375 | 10/1984 | Grollier | 252/542 |
| 4,578,216 | 3/1986 | Fujii et al. | 252/542 |

FOREIGN PATENT DOCUMENTS

| | | |
|---|---|---|
| 0154948 | 9/1985 | European Pat. Off. |
| 1371139 | 10/1963 | France |
| 2387031 | 11/1978 | France |
| 2512669 | 3/1983 | France |

*Primary Examiner*—Prince E. Willis
*Assistant Examiner*—James M. Silbermann
*Attorney, Agent, or Firm*—Oblon, Spivak, McClelland, Maier & Neustadt

[57] ABSTRACT

A composition for a hair treatment agent comprising as essential components: a chelating agent having a specific chelating value with respect to the chelation of the calcium ion, and a polymer compound selected from a group consisting of cationic polymers containing quaternary nitrogen, and peptides of an average molecular weight of 40 to 10,000, or their derivatives. The composition provides a perm-treatment with a good finishing effect by depressing absorption of calcium to the hair when it is perm-treated. It also serves as a shampoo, by further formulating an anionic or amphoteric surface active agent, which gives an excellent effect of suppleness and smoothness after washing and rinsing to hair which is damaged from a perm treatment.

3 Claims, No Drawings

COMPOSITION FOR HAIR TREATMENT AGENT

This application is a continuation of application Ser. No. 07/0122, filed on Nov. 19,1987, now abandoned.

BACKGROUND OF THE INVENTION

1. Field of the Invention:

This invention relates to a composition for a hair treatment agent and, more particularly, to a composition for a hair treatment agent which is capable of providing a perm-treatment with a good finishing effect such as a good feeling to touch and the least resistance to passage of a comb though the hair, by depressing absorption of calcium to the hair when it is perm-treated. The composition also provides an excellent effect of suppleness and smoothness after washing and rinsing to hair which is damaged from a perm treatment and the like, and improves the flexibility of the hair after drying by reducing the calcium throughout the hair.

2. Description of the Background:

Hair is easily damaged by external factors such as sun light, heat, chemical treatment, and mechanical stimulation, and fading of color, development of split hairs or deterioration of feeling to the touch occurs. Especially in the case where the hair has undergone a permanent wave treatment, it is known that because a reducing treatment is carried out by means of thioglycol acid followed by an oxidizing treatment by a bromate, the hair is hardened and the feel to the touch is considerably worsened.

Present inventors have found that such phenomena are caused by the release of amino acids and polypeptides from the hair, and also by the absorption of calcium by the hair during the perm treatment (the content of calcium becomes 3 to 5 times of the untreated hair after perm treatment.). It was also found that this increase of calcium takes place while rinsing the hair after the treatment by the reducing agent and the rinsing carried out after release of lot upon completion of the treatment by the oxydizing permanent wave agent.

On the other hand, in order to improve the feel of the hair, a rinse or treatment is used after shampooing, or a conditioning agent such as a cationic polymer is blended into the shampoo. However, hair which has undergone a permanent wave treatment is in a condition where adequate improvement in feel or where adequate restoration cannot yet be obtained. However, the state of arts in the conventional hair treatment agent cannot yet provide adequate improvement or restoration in feel.

In view of such a situation, the inventors of the present invention have carried out intensive studies, and as a result have discovered that the increase of calcium in the hair during permanent wave treatment and rinsing after that can be depressed by the use of a hair treatment agent formulated with a specific chelating agent and a specific polymer compound. The use of such hair treatment agent can also make up for amino acids and polypeptides lost from the hair by a permanent wave treatment. Such findings have led to the completion of the present invention.

SUMMARY OF THE INVENTION

Accordingly an object of this invention is to provide a composition for a hair treatment agent comprising as essential components: (A) a chelating agent wherein the chelating value with respect to the chelation of the calcium ion is greater than 230 mg $CaCO_3$/gm; and (B) a polymer compound selected from a group consisting of cationic polymers containing quaternary nitrogen, and peptides of an average molecular weight of 400 to 10,000, or their derivatives.

DETAILED DESCRIPTION OF THE INVENTION AND PREFERRED EMBODIMENTS

As a chelating agent which is suitable as the component (A) of the composition according to the present invention, it is desirable to have a chelating agent wherein the chelation value with respect to the chelation of the calcium ion expressed as milligrams of $CaCO_3$ per gram of chelating agent is greater than 230 mg $CaCO_3$/gm as determined by the following test method for carbonates (Hampshire Test).

Test Method for Carbonates

Exactly 200 gm of chelating agent are weighed out and dissolved in about 50 ml of distilled water. The pH is adjusted to about 8 using NaOH, after which 10 ml of 2% $Na_2CO_3$ is added, then the pH is adjusted to 11.0 with 0.1N NaOH, using a pH meter. The water is added to bring the volume up to 150 ml. This solution is then titrated with a solution containing 44.1 gm of calcium acetate monohydrate per liter, until a stable turbidity is confirmed.

During the titration, in order to avoid the threshold effect, 0.1 to 0.4 ml is added dropwise without agitation, after which the solution is adequately agitated. This procedure is repeated while the pH is maintained at 11.0 using 0.1N NaOH. The above calcium acetate solution is equivalent to 25 mg $CaCO_3$/l. The chelation value can be obtained from the following equation.

Chelation value (mg of $CaCO_3$/gm of chelating agent)

$$= \text{No. of mg of } CaCO_3 \text{ chelated per gm of chelating agent}$$

$$= 25 \times [\text{calcium acetate (ml)}]/\text{Weight of sample(gm)}$$

Following are examples of chelating agents which have a chelation value of 230 mg $CaCO_3$ per gram of chelating agent or higher.

| Chelating agent | Chelation Value (mg $CaCO_3$/gm) |
|---|---|
| 1-hydroxyhexane-1,1-diphosphonic acid | 280 |
| α-aminoethane-α,α-diphosphonic acid | 930 |
| α-aminobenzyl-α,α-diphosphonic acid | 1460 |
| Amino-tri(methylene phosphonic acid) | 820 |
| Ethylenediamine tetra(methylene phosphonic acid) | 860 |
| Nitriloacetic acid-di(methylene phosphonic acid) | 850 |
| N,N-diacetic acid-N-methylene phosphonic acid (Nitrilodiacetic acid - methylene phosphonic acid) | 540 |
| 1-hydroxyethane-1,1-diphosphonic acid | 810 |
| Phosphonic acetic acid | 270 |
| Citric acid | 328 |
| Diethylene triamino pentaacetic acid | 275 |
| 1,2-cyclohexane diamino tetraacetic acid | 285 |
| Ethylenediamine tetraacetic acid | 402 |
| Nitrilo triacetic acid | 578 |

These chelating agents can be used both independently or in mixtures of two or more types, blended in at 0.6% to 6% of the total shampoo composition, with the particularly desirable range being 0.8% to 2%.

In the present invention, among the polymer compounds used as the component (B), suitable cationic polymers are cationic cellulose derivatives, cationic starch, copolymers of diaryl quaternary ammonium salts and acryl amides, quaternary polyvinyl pyrrolidone derivatives, and the like.

As a cationic cellulose derivative, a compound which satisfies the following Formula 1 is desirable.

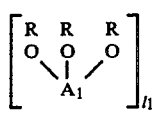

(1)

in which $A_1$ indicates a residual group of anhydroglucose units, and $l_1$ is an integer of from 50 to 20,000, and each R indicates the respective substitution group shown in the following formula (2):

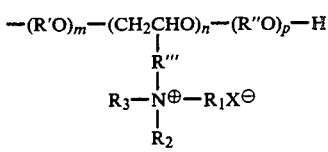

(2)

in which R' and R" represent alkylene groups with 2 or 3 carbon atoms, m is an integer from 0 to 10, n is an integer from 0 to 3, p is an integer from 0 to 10, R''' represents an alkylene group or hydroxyalkylene group with from 1 to 3 carbon atoms, $R_1$, $R_2$, $R_3$ may be the same or different, and represent an alkyl, aryl, or aralkyl group with less than 10 carbon atoms and which may form a heterocyclic ring with a nitrogen atom in the formula and X designates anion (chlorine, bromine, iodine, sulfuric acid, sulfonic acid, methyl-sulfuric acid, phosphoric acid, nitric acid, and the like.).

The degree of cation substitution of the cationic cellulose, that is, the average value of n for each anhydroglucose unit is preferably between 0.01 to 1, with the range of 0.02 to 0.5 being more preferable. Also, the total of m+p averages between 1 and 3. A substitution value of less than 0.01 is unsatisfactory, while if this value is 1 or greater there is no particular problem, but, from the aspect of reaction yield, a value below 1 is more desirable. The molecular weight of the cationic cellulose used here is in the range of about 100,000 to 3,000,000.

A desirable cationic starch for use in the present invention should satisfy the following formula (3):

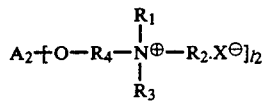

(3)

wherein $A_2$ represents a starch residual group, $R_4$ represents alkylene group or hydroxyalkylene group, $R_2$, $R_3$ may be the same or different, and represent an alkyl, aryl, or aralkyl group with less than 10 carbon atoms and which may form a heterocyclic ring with a nitrogen atom in the formula, X represents anion (chlorine, bromine, iodine, sulfuric acid, sulfonic acid, methyl-sulfuric acid, phosphoric acid, nitric acid, and the like.), and $l_2$ is a positive integer.

The degree of cation substitution of the cationic starch, i.e., number of cation groups for each anhydrous glucose group, is desirably 0.01 to 1, with more desirable range being 0.02 to 0.5, A substitution value of less than 0.01 is unsatisfactory, while if this value is 1 or greater there is no particular problem, but, from the aspect of reaction yield, a value below 1 is more desirable.

A desirable copolymer of diaryl quaternary ammonium salt and acryl amide, for use in the present invention should satisfy the following formulae (4) and (5).

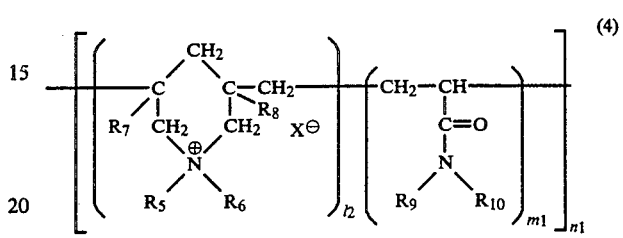

(4)

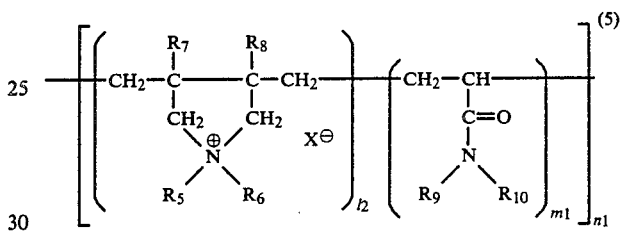

(5)

wherein $R_5$, $R_6$ may be the same or different groups from among the following - hydrogen, alkyl group (carbon atoms, 1 to 18), phenyl group, aryl group, hydroxy alkyl group, amidoalkyl group, cyanoalkyl group, alkoxyalkyl group, and carboalkoxyalkyl group, $R_7$, $R_8$, $R_9$, $R_{10}$ may be the same or different groups from among the following - hydrogen, lower alkyl group (carbon atoms, 1 to 3), phenyl group, X represents anion (chlorine, bromine, iodine, sulfuric acid, sulfonic acid, methyl-sulfuric acid, phosphoric acid, nitric acid, and the like.), $l_2$ is an integer from 1 to 50, $m_1$ is an integer from 1 to 50, and n1 is an integer from 150 to 8000.

The molecular weights of the copolymers of diaryl quaternary ammonium salts and acryl amides may be in the range from about 30,000 to 2,000,000, but the range from 100,000 to 1,000,000 is preferable.

A desirable quaternary polyvinyl pyrrolidone derivative or use in the present invention should satisfy the following formula (6).

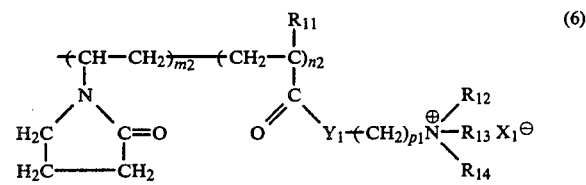

(6)

wherein $R_1$ represents a hydrogen atom or an alkyl group with 1 to 3 carbon atoms, $R_{12}$, $R_{13}$, and $R_{14}$ may be the same or different groups from among the following - hydrogen atoms, alkyl group with 1 to 4 carbon atoms, hydroxyalkyl group, amidoalkyl group, cyanoalkyl group, alkoxyalkyl group, and carboalkoxyalkyl group, $Y_1$ represents oxygen atom or NH group coupled with or amide, $X_1$ designates anion (chlorine, bromine, iodine, sulfuric acid, sulfonic acid, alkylsulfuric acid with 1 to 4 carbon atoms, phosphoric acid, nitric acid, and the like.), $p_1$ is an integer from 1 to 10, $m_2+n_2$ is an integer from 20 to 8000.

The molecular weights of the quaternary polyvinyl pyrrolidone derivative may be in the range from about 10,000 to 2,000,000, but the range from 50,000 to 1,500,000 is the most desirable.

The content of cationic nitrogen derived from the cationic polymer contained in the above-mentioned vinyl polymer is in the range from 0.004% to 0.2% by weight, with the most desirable range from 0.01% to 0.15% by weight. Below 0.004% the effect is inadequate; above 0.2% the performance is good, but the vinyl polymer becomes colored and the high cost is a disadvantage.

The peptide of an average molecular weight of 400 to 10,000 or its derivative in the (B) component or polymer compound can be hydrolyzed protein such as collagen, keratin, silk, soy protein, and the like. Here, the average molecular weight may be the weight average molecular weight, and suitable regulation is possible by carrying out an appropriate fractionation action or by the adjustment of the hydrolyzing conditions. All these can be manufactured by commonly known methods, or can be purchased as commercial products.

Following are several examples.

(1) Collagen hydrolyzate

There is no particular restriction on the collagen which can be used, but gelatin, glue, collagen fiber, collagen membrane, and the like are the preferred materials.

These collagens can be obtained from animal bones, connective tissue, and the like. For example, corium, internal membranes, tendons, cartilage, and the like, can all be used as raw materials to meet the objectives of the present invention. Commercial collagen hydrolyzate products which can be readily purchased are Bromois (Seiwa Kasei Co., Ltd.), Neutoran (Gruno Co.), Protein (Groder Co.), and the like.

(2) Keratin hydrolyzate

Examples of keratins which can be used are animal hair, human hair, feathers, animal claws, animal horns, hooves, fish scales, and the like. Especially desirable materials are wool, human hair, and feathers.

Suitable methods of hydrolysis are acid hydrolysis using hydrochloric acid, sulfuric acid, phosphoric acid, and the like; alkali hydrolysis using sodium hydroxide, sodium carbonate, and the like; and enzyme hydrolysis using protease. More details may be found in the methods described in Japanese Patent Laid-open No. 85308/1982.

(3) Silk hydrolyzate

Silk or silk fiber is made into a fine powder by means of an acid wash process and the hydrolyzed by acid or alkali hydrolysis, or enzyme.

Silk fiber hydrolyzates produced by acid hydrolysis using hydrochloric, sulfuric, or phosphoric acids and the like, or produced by alkali hydrolysis using sodium hydroxide, or sodium carbonate and the like, are all acceptable. In addition, enzyme hydrolysis can also be used jointly to give good results.

(4) Soy protein hydrolyzate

A suitable material can be manufactured by the process described in Japanese Patent Laid-open No. 85308/1982, for example. Suitable commercial products can also be procured. In addition, if the same results can be obtained, materials other than above-mentioned protein hydrolyzate, such as above-mentioned proteins or their derivatives, synthetic peptides, or natural peptides can be used without any additional treatment. As examples of proteins or the derivatives of proteins hydrolyzates, there are the keratin hydrolyzate derivatives described in Japanese Patent Publication 9600/1984.

These component (B) may be formulated in the hair treatment agent of this invention independently, or two or more kinds may be used in combination, in an amount preferably of 0.1 to 6% by weight, particularly preferably 0.5 to 2% by weight.

As desirable forms of the hair treatment agent of the present invention, there are shampoos, and the reducing and oxydizing agents of two-liquid type permanent wave agent. Followings are examples of desirable formulations of these hair treatment agents.

| | |
|---|---|
| Shampoo: | |
| Component (A) | 0.6–6% |
| Component (B) | 0.1–5% |
| Anoinic or amphoteric surface active agent | 5–30% |
| Component (C) | |
| Reducing permanent wave agent: | |
| Component (A) | 0.1–10% |
| Cationic polymer with quartenary nitrogen | 0.1–6% |
| Component (B') | |
| Reducing agent | adequate amount |
| Oxydizing permanent wave agent: | |
| Component (A) | 0.1–10% |
| Cationic polymer with quartenary nitrogen | 0.1–6% |
| Component (B') | |
| Oxidizing agent | adequate amount |

In the above compositions, the following anionic and amphoteric surface active agents are suitable as the surface active agent which is the component (B). Anionic surface active agents:

(1) A straight chain or branched chain alkylbenzenesulfonate with an alkyl group of an average of 10 to 16 carbon atoms.

(2) Alkyl or alkenyl ether sulfate with a straight chain or branched chain alkyl group or alkenyl group of an average of 10 to 20 carbon atoms, with the addition of ethylene oxide, propylene oxide, butylene oxide, ethylene oxide and propylene oxide in the ratio of from 0.1/9.9 to 9.9/0.1, or ethylene oxide and butylene oxide in the ratio of from 0.1/ 9.9 to 9.9/0.1, at an average of 0.5 to 8 mols per molecule.

(3) Alkyl or alkenyl sulfate with an alkyl group or alkenyl group of an average of 10 to 20 carbon atoms.

(4) Olefin sulfonate with an average of 10 to 20 carbon atoms per molecule.

(5) Alkane sulfonate with an average of 10 to 20 carbon atoms per molecule.

(6) Saturated or unsaturated fatty acids with an average of 10 to 24 carbon atoms per molecule.

(7) Alkyl or alkenyl ether carboxylate with an alkyl group or alkenyl group of an average of 10 to 20 carbon atoms, with the addition of ethylene oxide, propylene oxide, butylene oxide, ethylene oxide and propylene oxide in the ratio of from 0.1/9.9 to 9.9/0.1, or ethylene oxide and butylene oxide in the ratio of from 0.1/9.9 to 9.9/0.1, at an average of 0.5 to 8 mols per molecule.

(8) Salt or ester of α-sulfone fatty acid having an alkyl or alkenyl group with an average of 10 to 20 carbon atoms.

(9) N-acyl amino acid type surface active agents with an acyl group of 8 to 24 carbon atoms and free carboxylic acid radical group.

(10) Phosphoric acid monoester or diester type surface active agent with an alkyl group or alkenyl group of 8 to 24 carbon atoms.

Amphoteric surface active agents

(11) Secondary or tertiary amido-type imidazoline amphoteric surface active agents with an alkyl, alkenyl, or acyl group of 8 to 24 carbon atoms added to the α-position.

(12) Carbobetaine-, amidobetaine-, sulfobetaine-, hydroxysulfobetaine-, or amidosulfobetaine amphoteric surface active agents with an alkyl, alkenyl, or acyl group of 8 to 24 carbon atoms.

The counter ions to the anionic residual groups of these surface active agents can be alkali metal ions such as sodium and potassium, alkaline earth metal ions such as calcium and magnesium, ammonium ions, and alkanol amines with 1 to 3 alkanol groups of 2 or 3 carbon atoms (for example, monoethanolamine, diethanolamine, triethanol amine, tri-isopropanolamine, and the like). In addition, the counter ions to the cationic residual groups can be halogen ions such as chlorine, bromine, and iodine, as well as metasulfate and saccharinate ions.

Among these surface active agents, anionic surface active agents such as (2) alkyl ether sulfates, (3) alkyl sulfates, (4) olefin sulfonates, and (6) saturated or unsaturated fatty acids, as well as (11) secondary amido-type imidazoline amphoteric surface active agents are particularly desirable as the main active agents. Examples of preferable agents are polyoxyethylene lauryl ether sodium sulfate (an average of two or three mols ethylene oxide added), lauryl sulfuric triethanolamine, α-olefin sodium sulfonate (average 12 to 14 carbon atoms), and sodium salt of beef tallow/coconut oil (80/20)-fatty acid, and the like.

These surface active agents can be used both independently or in mixtures of two or more types, blended in preferably at 5% to 30% by weight of the total shampoo composition, with more desirable range being 10% to 25%.

Also, cationic polymers for the permanent wave reducing and oxydizing agents may be one type or in mixtures of two or more types, blended in at 0.1% to 6% by weight of the total permanent wave liquid, with a preferable range being 0.2 to 2%.

In addition, in the hair treatment composition of the present invention, components, other than the essential components, which are generally used in this type of composition may be blended as required depending on its formulation. Such components include, for example, humectants such as propylene glycol and glycerine; pH adjusting agents such as phosphoric and citric acids; viscosity adjusting agents such as ethanol, higher alcohols, hydroxymethyl cellulose, hydroxyethyl cellulose, hydroxypropyl cellulose, methyl cellulose, and the like; conditioning agents such as fats and oils, cationic surface active agents and the like; perfumes, pigments, ultraviolet ray absorbents, antioxidants, anti-dandruff agents, germicidal agents, antiseptics and the like. The balance of the shampoo is water which is used in the range of 30% to 97% by weight to make up the total of 100 parts by weight.

Many features of the invention will become apparent in the course of the following description of the exemplary embodiments which are given for illustration of the invention and are not intended to be limiting thereof.

EXAMPLES

In the examples below the following tests were used to evaluate the passage of fingers through the hair and softness imparted to the hair.

A tress made of human hair, 20 cm long, weighing 20 gm, was immersed for 10 minutes at 30° C. in a reducing permanent wave agent (a 7% aqueous solution of ammonium thioglycolate, adjusted to a pH of 9.0 with ammonia). Next, the tress was immersed for 10 minutes at 30° C. in the oxydizing agent (a 5% aqueous solution of sodium bromate), washed, then dried. This tress of hair which had been subjected to the permanent treatment was soaked in water at 40° C. One gram of the composition of the present invention was evenly worked through the tress, which was then lathered for one minute. The tress was then rinsed with an excess of water, after which its condition was evaluated with respect to ease of passage of fingers through the hair and softness, using the following standards.

Ease of passage of fingers through the hair when shampooed:

---
AAA: Good
BBB: Normal
CCC: Poor
Softness when shampooed:
AAA: Good softness
BBB: Normal softness
CCC: Hard
---

EXAMPLE 1

Shampoos having formulations shown in Table 1 were prepared according to a conventional method. The results of their evaluation are shown in Table 1.

In the examples below, the shampoo was adjusted to a pH of 7 and the blended amount is shown as the effective amount of each component.

Example 2

Shampoo compositions of the formulation in Table 2 were prepared and evaluated. The results are shown in Table 2.

EXAMPLE 3

Shampoo compositions of the formulation in Table 3 were prepared and evaluated. The results are shown in Table 3.

TABLE 1

| Detergent Composition | 1 | 2 | 3 | 4 | 5 | 6 | 7 | 8 |
|---|---|---|---|---|---|---|---|---|
| Sodium polyoxyethylene (2.5) | 20 | 20 | 20 | | | | | |

TABLE 1-continued

| Detergent Composition | 1 | 2 | 3 | 4 | 5 | 6 | 7 | 8 |
|---|---|---|---|---|---|---|---|---|
| lauryl sulfate | | | | | | | | |
| Triethanolamine polyoxyethylene (2.5) lauryl sulfate | | | | 20 | | | | |
| Triethanolamine lauryl sulfate | | | | | 20 | | | |
| Sodium α-oleffin sulfonate (C$_{14}$) | | | | | | 20 | | |
| Sodium lauroyl-N-methyl-β aranine | | | | | | | 20 | |
| Imidazoline type surface active agent * | | | | | | | | 20 |
| Lauric acid diethanolamide | 3 | 3 | 3 | 3 | 3 | 3 | 3 | 3 |
| Ethylene diamine tetraacetic acid | | | 1 | 1 | 1 | 1 | 1 | 1 |
| Cationized cellulose ** | | 1 | 1 | 1 | 1 | 1 | 1 | 1 |
| Ion-exchanged water | balance | balance | balance | balance | balance | balance | balance | balance |
| Ease of passage of fingers through the hair when shampooed | CCC | BBB | AAA | AAA | AAA | AAA | AAA | AAA |
| Softness when shampooed | CCC | CCC | AAA | AAA | AAA | AAA | AAA | AAA |

\* Miranol C2M conc. (sodium salt of sec-amido type imidazoline amphoteric surface active agent derived from coconut oil)
\*\* Polymer JR400 (manufactured by Union Carbide Corp.)

TABLE 2

| Detergent Composition | 9 | 10 | 11 | 12 | 13 | 14 | 15 | 16 |
|---|---|---|---|---|---|---|---|---|
| Sodium polyoxyethylene (2.5) lauryl sulfate | 20 | 20 | 20 | 20 | 20 | 20 | 20 | 20 |
| 1-hydroxyethane-1,1-diphosphonic acid | 0.1 | 0.5 | 1.0 | | | | | |
| Ethylenediamine tetraacetic acid | | | | 0.5 | 1.0 | | | |
| Citric acid | | | | | | 1.0 | | |
| Diethylenetriamine pentaacetic acid | | | | | | | 1.0 | |
| 1-hydroxyhexane-1,1-disulfonic acid | | | | | | | | 1.0 |
| Lauric acid diethanolamide | 3 | 3 | 3 | 3 | 3 | 3 | 3 | 3 |
| Cationized cellulose * | 1 | 1 | 1 | 1 | 1 | 1 | 1 | 1 |
| Ion-exchanged water | balance | balance | balance | balance | balance | balance | balance | balance |
| Ease of passage of fingers through hair when shampooed | BBB | BBB | AAA | BBB | AAA | AAA | AAA | AAA |
| Softness when shampooed | CCC | BBB | AAA | BBB | AAA | AAA | AAA | AAA |

\* Polymer JR400 (manufactured by Union Carbide Corp.)

TABLE 3

| Detergent Composition | 17 | 18 | 19 | 20 | 21 | 22 |
|---|---|---|---|---|---|---|
| Sodium polyoxyethylene (2.5) lauryl sulfate | 20 | 20 | 20 | 20 | 20 | 20 |
| Ethylenediamine tetraacetic acid | 1.0 | 1.0 | 1.0 | 1.0 | 1.0 | 1.0 |
| Cationized cellulose * | 0 | 0.1 | 0.5 | 1.0 | | |
| N,N-dimethyl-3,5-methylene pyperidinium chloride/acryl amide copolymer ** | | | | | 0.5 | |
| Ethosulfate salt of vinyl pyrrolidone/dimethylamino ethylacrylate copolymer *** | | | | | | 0.5 |
| Lauric acid diethanolamide | 3 | 3 | 3 | 3 | 3 | 3 |
| Ion-exchanged water | balance | balance | balance | balance | balance | balance |
| Ease of passage of fingers through hair when shampooed | BBB | AAA | AAA | AAA | AAA | AAA |
| Softness when shampooed | CCC | AAA | AAA | AAA | AAA | AAA |

\* Polymer JR400 (manufactured by Union Carbide Corp.)
\*\* Marquort 550 (manufactured by Merck Co.)
\*\*\* Gafcut 755N (manufactured by Gaf Co.)

EXAMPLE 4

Shampoo compositions (A) and (B) having the following formulations were prepared and subjected to hair-washing test by 20 women with permed hair. The results of the practical evaluation are shown in Table 4.

Shampoo A (Inventive Composition)

| | |
|---|---|
| Sodium polyoxyethylene (2.5) lauryl sulfate | 6 (%) |
| Imidazoline type surface active agent * | 6 |
| Sodium lauroyl-N-methyl-β-aranine | 6 |
| Antiseptic (methyl paraben) | 0.1 |
| 1-hydroxyethane-1,1-diphosphonic acid | 0.5 |
| Ethylenediamine tetra- | 0.5 |

-continued

| | |
|---|---|
| acetic acid | |
| Cationized cellulose ** | 1.0 |
| Perfume | 0.3 |
| Coloring agent | small amount |
| Water | balance (pH 7) |

Shampoo B (Comparative Composition)

| | |
|---|---|
| Sodium polyoxyethylene (2.5) lauryl sulfate | 6 (%) |
| Imidazoline type surface active agent * | 6 |
| Sodium lauroyl-N-methyl-β-aranine | 6 |
| Antiseptic (methyl paraben) | 0.1 |
| Perfume | 0.3 |
| Coloring agent | small amount |
| Water | balance (pH 7) |

* Polymer JR400
** Miranol C2M conc.

TABLE 4

| | Shampoo A feels better | Shampoo B feels better | Cannot differentiate |
|---|---|---|---|
| Foaming ability | 12 | 7 | 1 |
| Ease of passage of fingers through hair | 19 | 1 | 0 |
| Softness | 17 | 0 | 3 |
| Hair shape-up completeness | 18 | 1 | 1 |

EXAMPLE 5

Shampoo compositions of the formulation in Table 5 were prepared according to a conventional manner and evaluated. The results are shown in Table 5.

TABLE 5

| Detergent Composition | 1 | 2 | 3 | 4 | 5 | 6 | 7 | 8 |
|---|---|---|---|---|---|---|---|---|
| Sodium polyoxyethylene (2.5) lauryl sulfate | 20 | 20 | 20 | | | | | |
| Triethanolamine polyoxyethylene (2.5) lauryl sulfate | | | | 20 | | | | |
| Triethanolamine lauryl sulfate | | | | | 20 | | | |
| Sodium α-oleffin sulfonate (C$_{14}$) | | | | | | 20 | | |
| Sodium lauroyl-N-methyl-β aranine | | | | | | | 20 | |
| Imidazoline type surface active agent * | | | | | | | | 20 |
| Lauric acid diethanolamide | 3 | 3 | 3 | 3 | 3 | 3 | 3 | 3 |
| Ethylene diamine tetra-acetic acid | | 1 | 1 | 1 | 1 | 1 | 1 | 1 |
| Collagen hydrolyzate * | | 1 | 1 | 1 | 1 | 1 | 1 | 1 |
| Ion-exchanged water | balance | balance | balance | balance | balance | balance | balance | balance |
| Ease of passage of fingers through the hair when shampooed | CCC | BBB | AAA | AAA | AAA | AAA | AAA | AAA |
| Softness when shampooed | CCC | BBB | AAA | AAA | AAA | AAA | AAA | AAA |

* Miranol C2M conc. (sodium salt of sec-amido type imidazoline amphoteric surface active agent derived from coconut oil)
** NP 1000 (manufactured by Tanabe Pharmaceutical Co., Ltd.: Molecular weight: 1000)

EXAMPLE 6

Shampoo compositions of the formulation in Table 6 were prepared and evaluated. The results are shown in Table 6.

EXAMPLE 7

Shampoo compositions of the formulation in Table 7 were prepared and evaluated. The results are shown in Table 7.

EXAMPLE 8

Shampoo compositions of the formulation in Table 8 were prepared and evaluated. The results are shown in Table 8.

TABLE 6

| Detergent Composition | 9 | 10 | 11 | 12 | 13 | 14 | 15 | 16 |
|---|---|---|---|---|---|---|---|---|
| Sodium polyoxyethylene (2.5) lauryl sulfate | 20 | 20 | 20 | 20 | 20 | 20 | 20 | 20 |
| 1-hydroxyethane-1,1-diphosphonic acid | 0.1 | 0.5 | 1.0 | | | | | |
| Ethylenediamine tetra-acetic acid | | | | 0.5 | 1.0 | | | |
| Citric acid | | | | | | 1.0 | | |
| Diethylenetriamine pentaacetic acid | | | | | | | 1.0 | |
| 1-hydroxyhexane-1,1-disulfonic acid | | | | | | | | 1.0 |
| Lauric acid diethanolamide | 3 | 3 | 3 | 3 | 3 | 3 | 3 | 3 |
| Collagen hydrolyzate * | 1 | 1 | 1 | 1 | 1 | 1 | 1 | 1 |
| Ion-exchanged water | balance | balance | balance | balance | balance | balance | balance | balance |
| Ease of passage of fingers through hair when shampooed | CCC | BBB | AAA | BBB | AAA | AAA | AAA | AAA |
| Softness when shampooed | CCC | BBB | AAA | BBB | AAA | AAA | AAA | AAA |

* Nippi Pptide (manufactured by Nippi Co., Ltd.)

TABLE 7

| Detergent Composition | 17 | 18 | 19 | 20 | 21 | 22 | 23 |
|---|---|---|---|---|---|---|---|
| Sodium polyoxyethylene (2.5) lauryl sulfate | 20 | 20 | 20 | 20 | 20 | 20 | 20 |
| Ethylenediamine tetra-acetic acid | 1.0 | 1.0 | 1.0 | 1.0 | 1.0 | 1.0 | 1.0 |
| Collagen hydrolyzate (MW = 1500) | 0 | 0.1 | 0.5 | 1.0 | | | |
| Silk hydrolyzate (MW = 1500) | | | | | 0.5 | | |
| Soy protein hydrolyzate (MW = 1500) | | | | | | 0.5 | |
| Keratin hydrolyzate (MW = 1500) | | | | | | | 0.5 |
| Lauric acid diethanolamide | 3 | 3 | 3 | 3 | 3 | 3 | 3 |
| Ion-exchanged water | balance | balance | balance | balance | balance | balance | balance |
| Ease of passage of fingers through hair when shampooed | BBB | AAA | AAA | AAA | AAA | BBB | BBB |
| Softness when shampooed | CCC | BBB | AAA | AAA | AAA | BBB | BBB |

* MW = average molecular weight

TABLE 8

| Detergent Composition | 24 | 25 | 26 | 27 | 28 | 29 | 30 |
|---|---|---|---|---|---|---|---|
| Sodium polyoxyethylene (2.5) lauryl sulfate | 20 | 20 | 20 | 20 | 20 | 20 | 20 |
| Ethylenediamine tetra-acetic acid | 1.0 | 1.0 | 1.0 | 1.0 | 1.0 | 1.0 | 1.0 |
| Collagen hydrolyzate (MW = 200) | | | | | | 1.0 | |
| Collagen hydrolyzate (MW = 400) | 1.0 | | | | | | |
| Collagen hydrolyzate (MW = 1000) | | 1.0 | | | | | |
| Collagen hydrolyzate (MW = 1500) | | | 1.0 | | | | |
| Collagen hydrolyzate (MW = 2000) | | | | 1.0 | | | |
| Collagen hydrolyzate (MW = 10000) | | | | | 1.0 | | |
| Collagen hydrolyzate (MW = 100000) | | | | | | | 1.0 |
| Lauric acid diethanolamide | 3 | 3 | 3 | 3 | 3 | 3 | 3 |
| Ion-exchanged water | balance | balance | balance | balance | balance | balance | balance |
| Ease of passage of fingers through hair when shampooed | BBB | AAA | AAA | AAA | BBB | CCC | CCC |
| Softness when shampooed | BBB | AAA | AAA | AAA | BBB | CCC | CCC |

* MW = average molecular weight

EXAMPLE 9

Shampoo compositions (A) and (B) having the following formulations were prepared and subjected to hair-washing test by 20 women with long hair. The results of the practical evaluation are shown in Table 9.

| Shampoo A (Inventive Composition) | |
|---|---|
| Sodium polyoxyethylene (2.5) lauryl sulfate | 6 (%) |
| Imidazoline type surface active agent * | 6 |
| Sodium lauroyl-N-methyl-β-aranine | 6 |
| Antiseptic (methyl paraben) | 0.1 |
| 1-hydroxyethane-1,1-diphosphonic acid | 0.5 |
| Ethylenediamine tetra-acetic acid | 0.5 |
| Collagen hydrolyzate ** | 1.0 |
| Perfume | 0.3 |
| Coloring agent | small amount |
| Water | balance (pH 7) |

| Shampoo B (Comparative Composition) | |
|---|---|
| Sodium polyoxyethylene (2.5) lauryl sulfate | 6 (%) |
| Imidazoline type surface active agent * | 6 |
| Sodium lauroyl-N-methyl-β-aranine | 6 |
| Antiseptic (methyl paraben) | 0.1 |
| Perfume | 0.3 |
| Coloring agent | small amount |
| Water | balance (pH 7) |

* Miranol C2M conc.
** Nippi Peptide PA-15L

TABLE 9

| | Shampoo A feels better | Shampoo B feels better | Cannot differentiate |
|---|---|---|---|
| Foaming ability | 12 | 7 | 1 |
| Ease of passage of fingers through hair | 19 | 1 | 0 |
| Softness | 17 | 0 | 3 |
| Hair shape-up completeness | 18 | 1 | 1 |

EXAMPLE 10

Permanent wave liquids with the following formulations were prepared, and after perm treatment using them feel to the touch was evaluated. In addition, the calcium content of the hair was analyzed quantitatively to determine the calcium absorption inhibitive effect. The results are shown in Table 10. In the examples below, the formulated amount of each component is shown by the effective amount, and all the reducing permanent wave agents are adjusted to a pH of 8.1 by an aqueous solution of ammonia.

Formulation

| Inventive Product No. 1 | |
|---|---|
| Reducing agent: | |
| Ammonium thioglycolate | 6.8% |
| Ammonium bicarbonate | 2.5% |
| Ethylenediamine tetra-acetic acid | 0.5% |
| Aqueous ammonia | 1.9% |
| Dimethyldiallyl ammonium chloride homopolymer * | 0.2 |
| Coloring agent | suitable amount |
| Perfume | suitable amount |
| Purified water | balance |
| Total | 100% |
| Oxydizing agent: | |
| Sodium hydrobromide | 8.0% |
| Ethylenediamine tetra-acetic acid | 0.5% |
| Cationized cellulose ** | 0.5% |
| Antiseptic | suitable amount |
| Purified water | balance |
| Total | 100% |

* Merck Co. Marquart 100
** Union Carbide Corp. Polymer JR-400

COMPARATIVE PRODUCT

Compositions excluding ethylenediamine tetraacetic acid, dimethyldiallyl ammonium chloride homopolymer, and cationized cellulose from the above Inventive Composition were used as Comparative Compositions.

Evaluation of feelings to the touch

A tress made of virgin hair, 10 cm×5 cm and 15 cm long, was rinsed under prescribed conditions and dried. It was then immersed in purified water, a lot was wound around it, to which a reducing permanent wave agent was applied. After having been left for 20 minutes, the tress was washed, water was wiped off, and the oxydizing agent was applied. After it was left for 10 minutes and after lot was removed from it, the tress was washed and subjected to evaluation with respect to feelings to the touch. The following symbols apply to the designation of the results:

AAA: A comb passes through the hair very easily, and there is no feeling of hardness.
BBB: A comb passes through the hair with ease. Hardness of the hair is hardly felt.
CCC: A comb does not passes through the hair with ease, and the hair is felt hard.

Measurement of Calcium

The perm-treated hair was released from a lot, washed, and 1 mg of the washed hair weighed precisely was put into a 20 ml sample bottle, to which 10 ml of a 0.5N hydrochloric acid was added. After the hair having been immersed in the hydrochloric acid solution, the extract was subjected to determination of calcium content by means of ICP emission spectrochemical analysis. The results are shown in Table 10.

TABLE 10

| | Calcium content | Feeling to touch |
|---|---|---|
| Inventive Product No. 1 | 880 ppm | AAA |
| Comparative Product No. 1 | 2850 ppm | CCC |

Hair treated by the inventive product has a less adsorbed calcium content and provides ease of passage of a comb, without feeling of hardness.

EXAMPLE 11

Permanent wave agents were prepared according to the formulations of the reducing and oxydizing agents of Example 10, except that chelating agents listed in Table 11 were used instead of ethylenediamine tetraacetic acid in the amount of 0.5% in these regents.

Each sample was subjected to the evaluation with respect to the feeling to touch in the same manner as in Example 10. The results are shown in Table 11. As a comparative product, a composition with the formulation as the inventive products in Example 10 but for inclusion of ethylenediamine tetraacetic acid was used.

TABLE 11

| | Chelating agents | Amount formulated | Feeling to touch |
|---|---|---|---|
| Inventive Products | | | |
| No. 1 | ethylenediamine tetraacetic acid | 0.5 | AAA |
| No. 2 | ethylenediamine tetraacetic acid | 0.1 | BBB |
| No. 3 | ethylenediamine tetraacetic acid | 1.0 | AAA |
| No. 4 | nitrilo triacetic acid | 0.5 | BBB |
| No. 5 | 1,2-cyclohexanediamine tetaacetic acid | 0.5 | AAA |
| No. 6 | 1-hydroxyethane-1,1-diphosphonic acid | 0.5 | AAA |
| No. 7 | diethylenetriamine pentaacetic acid | 0.5 | AAA |
| No. 8 | 1-hydroxyhexane-1,1-diphosphonic acid | 0.5 | AAA |
| No. 9 | α-aminoethane α,α-diphosphonic acid | 0.5 | BBB |
| No. 10 | α-aminobenzyl α,α-diphosphonic acid | 0.5 | BBB |
| No. 11 | aminotri(methylenephosphonic acid) | 0.5 | BBB |
| No. 12 | ethylenediaminetetra (methylenephosphonic acid) | 0.5 | BBB |
| No. 13 | nitrilo triacetic acid-methylenephosphonic acid | 0.5 | BBB |
| No. 14 | nitrilo acetic acid-dimethylenephosphonic acid | 0.5 | BBB |
| No. 15 | phosphono acetic acid | 0.5 | BBB |
| Comparative Product | non | — | CCC |

Hairs treated by inventive products have a less adsorbed calcium content and provide ease of passage of a comb, without feeling of hardness.

EXAMPLE 12

Compositions were prepared by formulating the chelating agent (ethylenediamine tetraacetic acid) in compositions of Example 10 and a cationic polymer (dimethyldiallyl ammonium chloride homopolymer, cationized cellulose) as shown in Table 12. The compositions were subjected to evaluation with respect to the calcium content and the feeling to touch.

The results are shown in Table 12.

TABLE 12

| | Reducing permanent wave agent | | Oxydizing permanent wave agent | | Calcium content (%) | Feeling to touch |
|---|---|---|---|---|---|---|
| | Chelating agent 0.5% (ethylenediamine tetraacetic acid) | Cationic polymer 0.2% (dimethyldiallyl ammonium homopolymer) | Chelating agent 0.5% (ethylenediamine tetraacetic acid) | Cationic polymer 0.2% (cationized cellulose) | | |
| Inventive Product | | | | | | |
| No. 1 | + | + | + | + | 880 | AAA |
| No. 16 | + | + | − | − | 1234 | BBB |
| No. 17 | + | + | + | − | 1020 | BBB |
| No. 18 | − | − | + | + | 1277 | BBB |
| No. 19 | − | + | + | + | 1062 | BBB |
| Comparative Product | | | | | | |
| No. 1 | − | − | − | − | 2850 | CCC |
| No. 3 | + | − | − | − | 2283 | CCC |
| No. 4 | − | + | − | − | 2208 | CCC |
| No. 5 | − | − | − | − | 2341 | CCC |
| No. 6 | − | − | − | − | 2326 | CCC |

As can be seen from Table 12, the compositions for reducing and oxydizing permanent wave agents added with the chelating agent and cationic polymer exhibited resistance to passage of comb through the hair and had feeling of hardness, while those added with the chelating agent and cationic polymer exhibited ease of passage of a comb without feeling of hardness.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A shampoo composition comprising as essential components:
   (A) from 0.6 to 6% by weight of at least one chelating agent selected from the group consisting of α-aminoethane-α, α-diphosphonic acid, α-aminobenzyl-α, α-diphosphonic acid, amino-tri(methylene phosphonic acid), ethylene diamine tetra(methylene phosphonic acid), nitriloacetetic acid-di(methylene phosphonic acid), N,N-diacetic acid-N-methylene phosphonic acid, 1-hydroxyethane-1,1-diphosphonic acid, ethylenediamine tetraacetic acid, and nitrilo triacetic acid,
   (B) from 0.1 to 5% be weight of at least one polymeric compound selected from the group consisting of cationic polymers containing quaternary nitrogen, and peptides of an average molecular weight of 400 to 10,000 or their derivatives, and
   (C) from 5 to 30% by weight of at least one surface active agent selected from the group consisting of anionic and amphoteric active agents.

2. The shampoo composition of claim 1, wherein the polymeric compound (B) is a cationic polymer containing quaternary nitrogen.

3. The shampoo composition of claim 1, wherein the polymeric compound (B) is a peptide of an average molecular weight of 400 to 10,000.

* * * * *